United States Patent
Choi et al.

(10) Patent No.: US 9,173,588 B2
(45) Date of Patent: Nov. 3, 2015

(54) METHOD FOR IDENTIFYING STIMULATION TARGET

(71) Applicant: National Chiao Tung University, Hsinchu (TW)

(72) Inventors: Charles Tak Ming Choi, Hsinchu (TW); Shu-Hai Sun, Hsinchu (TW); Yi-Hsuan Lee, Hsinchu (TW)

(73) Assignee: National Chiao Tung University, Hsinchu (TW)

( * ) Notice: Subject to any disclaimer, the term of this patent is extended or adjusted under 35 U.S.C. 154(b) by 0 days.

(21) Appl. No.: 13/628,701

(22) Filed: Sep. 27, 2012

(65) Prior Publication Data
US 2013/0085362 A1 Apr. 4, 2013

(30) Foreign Application Priority Data
Sep. 30, 2011 (TW) .............................. 100135451 A

(51) Int. Cl.
| | |
|---|---|
| *A61B 6/03* | (2006.01) |
| *A61B 5/055* | (2006.01) |
| *A61N 1/05* | (2006.01) |
| *A61B 5/053* | (2006.01) |
| *A61B 6/12* | (2006.01) |

(52) U.S. Cl.
CPC ............. *A61B 5/0536* (2013.01); *A61B 5/0538* (2013.01); *A61B 6/032* (2013.01); *A61B 6/12* (2013.01)

(58) Field of Classification Search
CPC .... A61B 5/0536; A61B 5/0538; A61B 6/032; A61B 6/12
USPC ......... 600/547, 377, 426, 407, 202, 310, 473; 607/3, 59, 116, 72, 45, 122, 554, 62, 607/117–118; 382/131
See application file for complete search history.

(56) References Cited

U.S. PATENT DOCUMENTS

| | | | | |
|---|---|---|---|---|
| 5,465,730 | A  * | 11/1995 | Zadehkoochak et al. | 600/547 |
| 6,201,990 | B1 * | 3/2001 | Wexler et al. | 600/547 |
| 6,301,492 | B1 * | 10/2001 | Zonenshayn | 600/378 |
| 8,452,415 | B2 * | 5/2013 | Goetz et al. | 607/116 |
| 2007/0203545 | A1 * | 8/2007 | Stone et al. | 607/59 |
| 2009/0149898 | A1 * | 6/2009 | Hulvershorn et al. | 607/3 |
| 2010/0100152 | A1 * | 4/2010 | Martens et al. | 607/45 |
| 2010/0198315 | A1 * | 8/2010 | Martens et al. | 607/72 |
| 2013/0085361 | A1 * | 4/2013 | Mercanzini et al. | 600/377 |

* cited by examiner

*Primary Examiner* — Michael Rozanski
(74) *Attorney, Agent, or Firm* — Mintz Levin Cohn Ferris Glovsky and Popeo, P.C.; Peter F. Corless; Steven M. Jensen

(57) ABSTRACT

A method for identifying a stimulation target is provided, which uses microelectrode recording and electrical impedance tomography techniques together in a composite probe. The composite probe includes at least a microelectrode recording sensor and a plurality of microelectrodes, so that after the composite probe is guided and implanted to a depth suitable for the stimulation target based on microelectrode recording signals, tissue structures surrounding the composite probe are delineated by using the plurality of microelectrodes, and the boundary of the stimulation target and the precise location of the composite probe within the stimulation target are determined. Accordingly, the present invention provides a quick and accurate direction for surgeons, eliminating the problem of not knowing the exact location of the implanted probe within the stimulation target as in the case during deep brain stimulation surgeries.

14 Claims, 7 Drawing Sheets

METHOD FOR IDENTIFYING STIMULATION TARGET

CROSS-REFERENCES TO RELATED APPLICATIONS

This application claims under 35 U.S.C. §119(a) the benefit of Taiwanese Application No. 100135451, filed Sep. 30, 2011, the entire contents of which is incorporated herein by reference.

FIELD OF THE INVENTION

The present invention relates to a method for identifying stimulation targets, and more particularly, to a method for identifying stimulation targets applicable to deep brain stimulation (DBS).

BACKGROUND OF THE INVENTION

Side effects often appear after patients have taken medicines, and one of the most common side effects is dyskinesia, which not only hinders a normal life, and may also induce a variety of symptoms of Parkinson's disease.

In addition to drug-induced side effects, after the drug has been taken for a long period of time, it may often lose efficacy and often induce an "on-off" alternating reaction. When the drug induces the "on" reaction, the patient's symptom is under control, but when the "off" reaction is induced, the patient's symptoms will not be able to be controlled, and thus the ability to lead a normal life is affected.

Therefore, when the patient cannot carry out normal activities or quality of life is affected due to the above two reasons (the side effects of drugs and the "on-off" alternating reaction), surgical treatments would need to be considered. Such surgeries can be divided into two main types: deep brain stimulation (DBS) and lesion procedure which involves a higher risk, among which deep brain stimulation is more popular.

In the current deep brain stimulation surgery, microelectrode recording (MER) is employed to help determine the implant position for a permanent wire that is used to stimulate the target within the brain by electricity. Specifically, this technique first uses Computed Tomography (CT) scanning and Magnetic Resonance Imaging (MRI) to search for a rough position of the target to obtain a first implantation trajectory for implanting a probe with a microelectrode recording sensor. This sensor performs microelectrode recording to confirm whether the probe has reached the pre-defined position of the stimulation target. If the first implantation of the probe position is not satisfactory, then the probe is taken out and implanted in a different trajectory, until the probe is successfully implanted in the predefined target position. When the depth of probe implanted has reached the stimulation target, the probe can then be removed and replaced with a permanent wire. However, the microelectrode recording technique can be used only to determine whether the depth of implanted probe has reached the stimulation target, but cannot be used to determine the exact location of the probe within the stimulation target. Therefore, it is possible that the permanent wire is placed at the non-optimal position within the stimulation target rather than being properly implanted at the "optimal location" within the stimulation target. If the placement position is not ideal for the permanent wire, the part of the target within the brain that is stimulated upon electrical conduction will be limited, and thus cannot achieve the desired effect of the surgery.

U.S. Pat. No. 6,301,492 discloses an integrated probe applicable to DBS surgery, which integrates a DBS wire into a probe with a microelectrode recording sensor, so that after the probe is implanted into the stimulation target, the probe is not removed and replaced by a permanent wire, this can reduce the complexity of the surgery. However, this prior-art technique still cannot determine if the implant position of the probe is accurate or not, so several trajectories for implanting the probe may still be required to locate the best implant position, so a fast and accurate implantation of the probe into the desired location of the stimulation target is not possible, which increases the burden on the patient and surgical risks of failure.

Referring to FIG. 1, an existing electrical impedance tomography (EIT) technique is shown. As shown, a wire with electrodes 1-16 is dispose around the periphery of a specific region 100. Through electrodes 1 and 3 on the surface of this specific region 100, a current source 104 may input signals into the specific region 100. In the meantime, the presence of a conductive target 102 will affect the electric field profile of 100, that is, the equipotential line 108 will be altered with the presence of 104 which reflects on the potential measured by electrodes 4-16 on the surface of the specific region 100. A voltage measuring device 106 is used for receiving signals to calculate the impedances within the specific region 100 and reconstruct the image of the conductive target 102 in the specific region 100. For example, the voltage measuring device 106 first connects to the electrodes 6 and 8, after receiving signals from the electrodes 6 and 8, it subsequently moves to measure voltage signals from other pairs of electrodes. In short, the electrical impedance tomography technique surrounds the target with electrodes, and performs some established voltage measuring procedures to delineate the location of the target within the region surrounded by the electrodes. As for DBS surgeries, it is different from the above technique in that the electrode is implanted into the brain toward the target. If one wishes to delineate the tissue structures surrounding of the probe in a DBS surgery so as to know the precise location of the probe implanted in the target, the electrical impedance tomography technique is not directly applicable.

SUMMARY OF THE INVENTION

In light of forgoing drawbacks, an objective of the present invention is to provide a method for efficiently and quickly identifying the boundary of the stimulation target and precise positions of the implanted probes, thereby increasing accuracy of each probe insertion during the surgeries, and overcoming the drawback of not knowing the precise locations of the probes within the stimulation target using the MER technique.

In accordance with the above and other objectives, the present invention provides a method to identify the stimulation target, comprising the following steps: performing Computed Tomography (CT) scanning and Magnetic Resonance Imaging (MRI) on a specific region inside a patient to obtain a first implantation trajectory for the specific region; implanting a first composite probe into the specific region based on the first implantation trajectory to obtain microelectrode recording signals via the first composite probe, and thereby enabling the first composite probe to be guided into a predefined depth within a stimulation target of the patient based on the microelectrode recording signals; enabling the first composite probe to inject electrical current into tissue structures surrounding the first composite probe and use a plurality of electrodes in the first composite probe to measure a first electrical potential, and converting the first electrical potential into a first image that delineates the tissue structures surrounding the first composite probe; and identifying the boundary of the stimulation target and pin-pointing a location of the first composite probe implanted within the stimulation target according the first image.

Moreover, the present invention also provides a method for identifying the stimulation target, comprising the steps of: performing Computed Tomography (CT) scanning and Magnetic Resonance Imaging (MRI) on a specific region inside a patient to obtain a first implantation trajectory suitable for this specific region; implanting a plurality of composite probes into the specific region based on the first implantation trajectory using the microelectrode recording signals obtained via the plurality of composite probes, and thereby enabling the plurality of composite probes to be guided into predefined depths within a stimulation target of the patient based on the microelectrode recording signals; enabling the plurality of composite probes to inject a plurality of electrical currents into tissue structures surrounding the composite probes and measure a plurality of electrical potentials, and converting the plurality of said electrical potentials into a plurality of images that delineate the tissue structures surrounding the composite probes; and identifying the boundary of the stimulation target and pin-pointing a locations of the composite probes implanted within the stimulation target according to the plurality of images.

Compare to the prior art, the present invention not only uses the MER signals for guidance, but also applies the image conversion technique to delineate the tissue structures surrounding the composite probes; therefore, the boundary and the precise locations of the composite probes within the stimulation target can be quickly and efficiently identified, thereby allowing the permanent wire to be accurately implanted into the optimal location of the stimulation target and achieving the expected efficacy.

BRIEF DESCRIPTION OF THE DRAWINGS

The present invention can be more fully understood by reading the following detailed description of the preferred embodiments, with reference made to the accompanying drawings, wherein.

DETAILED DESCRIPTION OF THE EMBODIMENTS

The present invention is described by the following specific embodiments. Those with ordinary skills in the arts can readily understand the other advantages and functions of the present invention after reading the disclosure of this specification. The present invention can also be implemented with different embodiments. Various details described in this specification can be modified based on different viewpoints and applications without departing from the scope of the present invention.

Figure 1:
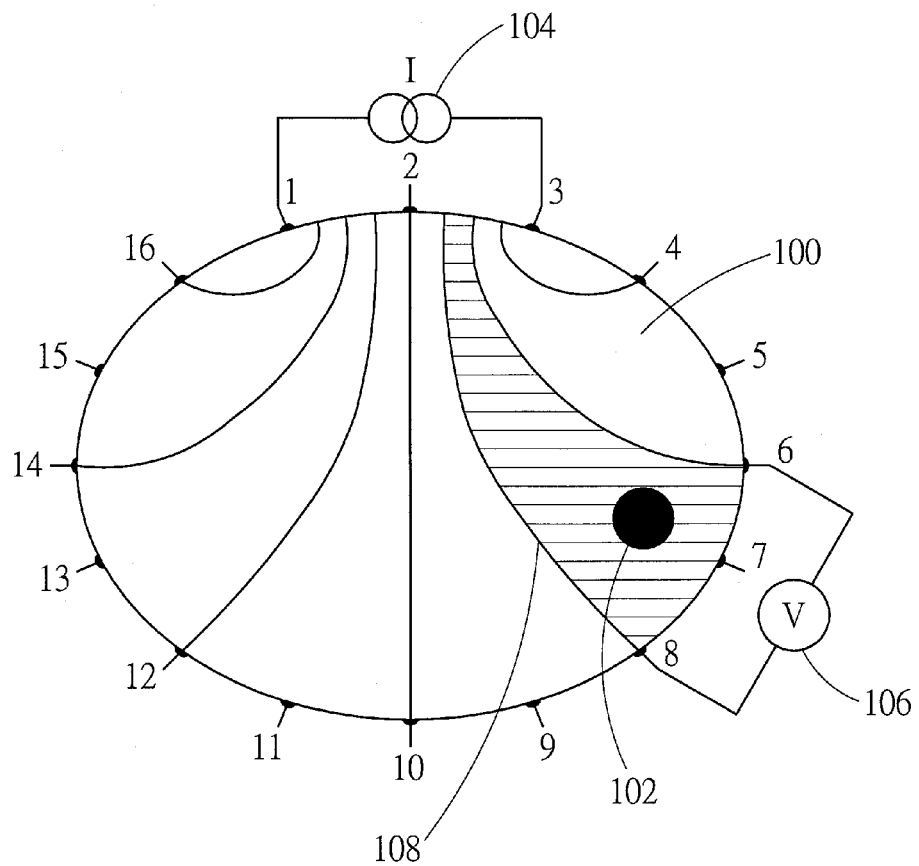
FIG. 1 is a 2D plane illustrating the existing EIT technique.
Figure 2:
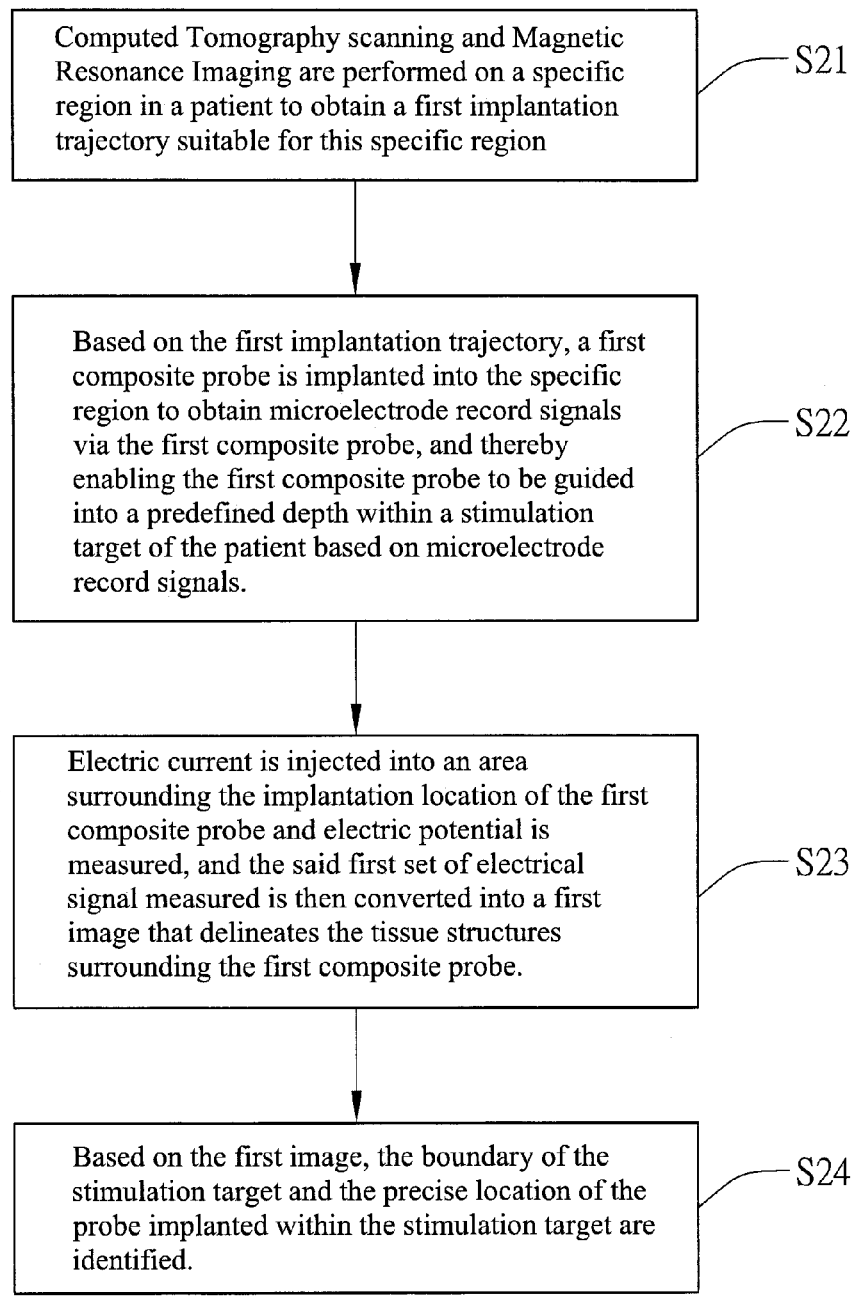
FIG. 2 is a flowchart illustrating the method for identifying a stimulation target according to an embodiment of the present invention.

The steps of method for identifying the stimulation target applicable to deep brain stimulation (DBS) according to an embodiment of the present invention are shown in FIG. 2.

As shown, in step S21, Computed Tomography (CT) scanning and Magnetic Resonance Imaging (MRI) are performed on a specific region in the patient to obtain a first implantation trajectory suitable for this specific region, then step S22 is performed.

In an embodiment of the present invention, step S21 can be implanted by using medical equipments such as a stereotactic frame, a CT scanning device, and a magnetic resonance imaging device. The specific region is a brain. For example, the stereotactic frame is used for identifying the head, and the CT device and magnetic resonance imaging device are used for performing CT scanning and magnetic resonance on the brain to obtain a CT scan image and a magnetic resonance image, and then the first implantation trajectory is obtained based on analyzing the computed tomography scan image and the magnetic resonance image.

In step S22, based on the first implantation trajectory obtained in step S21, a first composite probe that can be connected to a signal generating and receiving device is implanted into the specific region, so that microelectrode recording (MER) signals can be obtained by the signal generating and receiving device via the first composite probe, such that the first composite probe is guided based on the microelectrode recording signals into a predefined depth of a stimulation target in the patient. Then, step S23 is performed.

In an embodiment of the present invention, the first composite probe includes at least a microelectrode recording signal sensor for measuring the microelectrode recording signals, and a plurality of electrodes for injecting a first electrical current and measuring electrical potential signal. The plurality of electrodes is arranged in an electrode array, a specific structure thereof is disclosed in abovementioned U.S. Pat. No. 6,301,492. The signal generating and receiving device can be separate signal generating and signal receiving devices.

In step S23, electrical current is injected into the region surrounding the composite probe and electrical potential is measured through the composite probe according to a relevant electrical impedance tomography (EIT) algorithm or device using the first composite probe to generate a first image that delineates the tissue structures surrounding the first composite probe. Then, step S24 is performed.

In step S24, based on the first image, the precise location of the probe relative to the stimulation target is determined, which is used for subsequent implantation of a permanent wire. Of course, the implantation trajectory for subsequent implantation of the permanent wire within the patient is also determined at the same time.

Moreover, if the implantation position of the first composite probe is not satisfactory, or the boundary of the stimulation target is to be further determined, after step S23, a step S23-1 (not shown) and a step S23-2 (not shown) can be optionally performed.

In step S23-1, a second composite probe is implanted through another trajectory based on the first image of the tissue structures surrounding the first composite probe, and is implanted to a predefined depth of the stimulation target in the same manner as that carried out in step S22. Then, step S23-2 is performed. In an embodiment of the present invention, the structure of the second composite probe can be the same as that of the first composite probe. The first composite probe can be kept in the patient or withdraw from the patient.

In step 23-2, electrical current is injected into the tissue structures surrounding the second composite probe and electrical potential is measured, and the said measured data is used to generate a second image that delineates the tissue structures surrounding the second composite probe. Then, in step S24, based on the first and the second images, the boundary of the stimulation target can be determined for subsequent implantation of a permanent wire.

Needless to say, the generation of the second image need not only be based on electrical signal injected and measured by the second composite probe alone on the surrounding tissue structures, but also by both the first (if the first composite probe is kept in the patient) and the second composite probes. By increasing the number of stimulating electrodes, the resolution of the second image is increased, and the boundary of the stimulation target can be more clearly defined.

It should be noted that in actual implantation of the step of converting the first and the second electrical current injected and electrical potential measured into images, a current, voltage and impedance characteristic analysis of the specific region can first be performed based on the first and the second electrical current injected and electrical potential measured; then the result of the current, voltage and impedance characteristic analysis is used to generate the first or the second image that delineates the tissue structures surrounding the first or the second composite probe.

In order to understand more fully the implementation details of the above steps S21 to S24, the following descriptions in conjunction with the drawings are given.

Figure 3A:
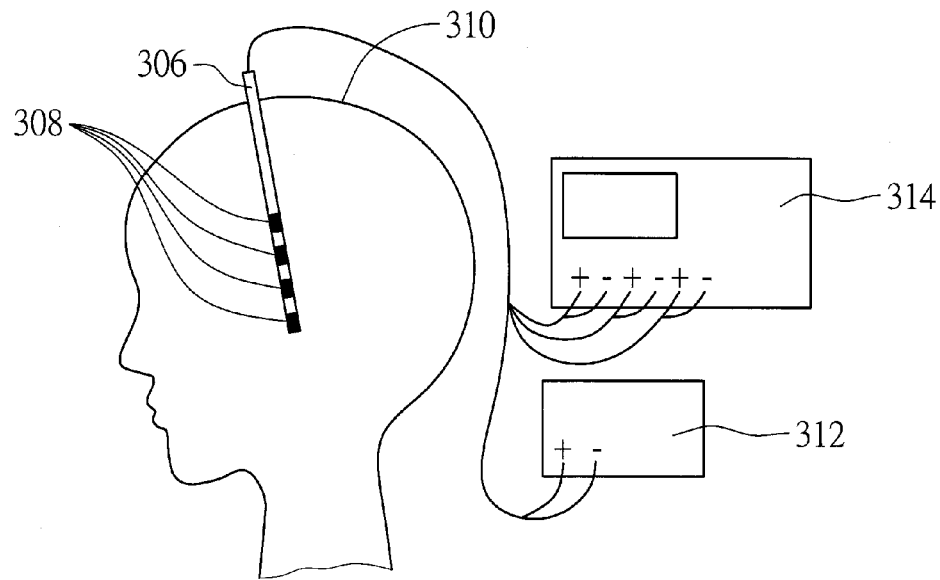
FIGS. 3A, 3B and 3C are cross-sectional diagrams depicting composite probe(s) implanted in the target within the brain according to an embodiment of the present invention.
Figure 3B:
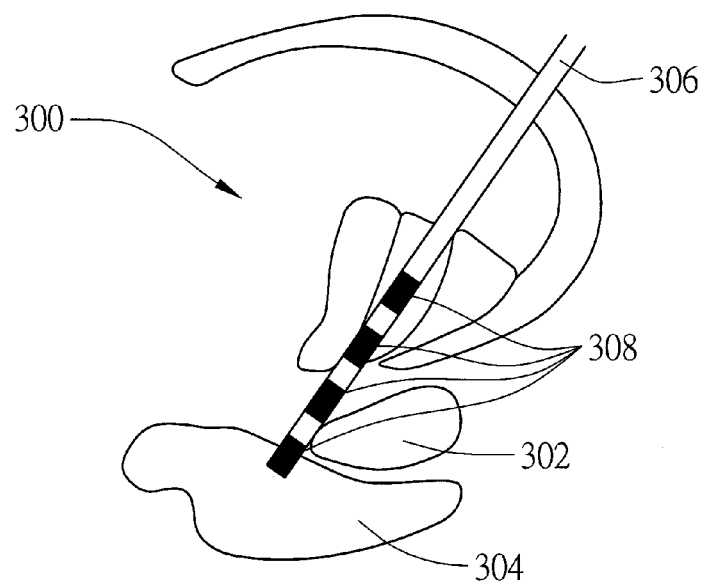

It should be noted that FIG. 3A is a schematic diagram depicting a first composite probe implanted in a brain; FIG. 3B is a schematic diagram depicting partial enlarged region of FIG. 3A; and FIG. 3C is a schematic diagram depicting first and second composite probes implanted in a target within the brain.

As shown in FIG. 3A, a first composite probe 306 is implanted into a brain 310 according to the first implantation trajectory obtained in step S21, and microelectrode recording signals are then generated based on a MER sensor (not shown) in the first composite probe 306, which guides the first composite probe 306 to be implanted into a predefined depth in the stimulation target in the brain 310, and the first composite probe 306 is connected with a signal generator 312 (as a current source) and a signal receiver 314 (for voltage measurements).

Moreover, as shown in FIG. 3B, the brain 310 has the thalamus 300. The thalamus 300 has the subthalamic nucleus (STN) 302 and the substantia nigra reticulate (SNr) 304 below the STN 302. Assuming the STN 302 is the stimulation target of the present application, after the first composite probe 306 is implanted into a certain depth appropriate for the STN 302 of the brain 310, an electrical impedance tomography (EIT) device (not shown) performs the EIT analysis on a plurality of electrodes 308 on the first composite probe 306; that is, electrical current is injected and electrical potential is measured by the first composite probe 306 on the tissue structures surrounding the composite probe, the first electrical signal measured is then converted to the first image that delineates the tissue structures surrounding the first composite probe 306, and thus the precise location and implantation trajectory of the first composite probe in the stimulation target can be determined based on the first image.

Figure 3C:
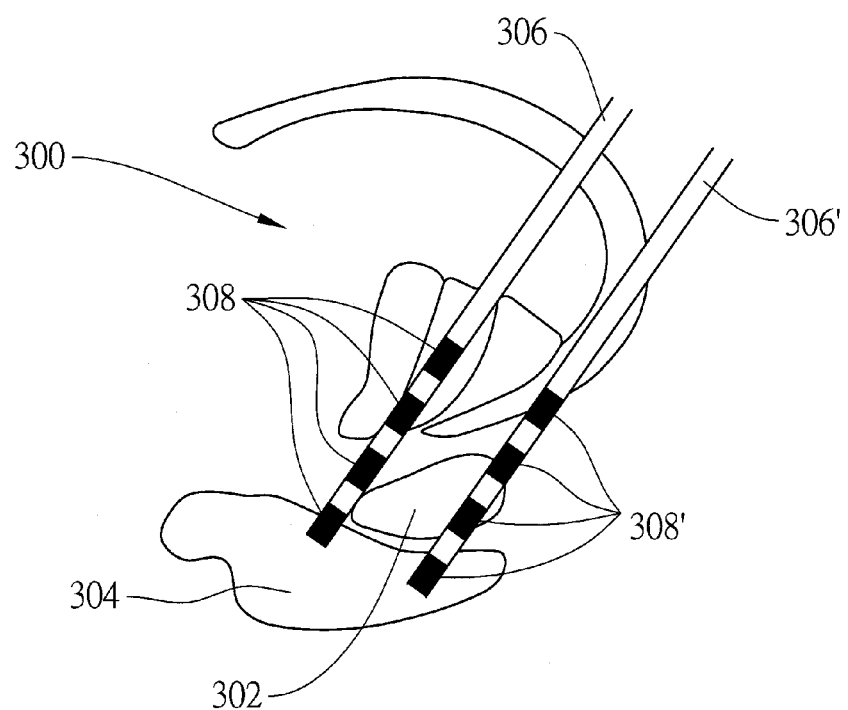

Furthermore, as shown in FIG. 3C, in order to more precisely define the boundary of the stimulation target, the step S23-1 and step S23-2 can be further optionally performed, in which, a second composite probe 306' is implanted into the brain 310 based on the first image of the tissue structures delineated in step S23 to a predefined depth of the stimulation target in a the same manner as that carried out in step S22.

After the second composite probe 306' is implanted into the brain 310, the EIT device may, using a plurality of electrodes 308' on the second composite probe 306', inject a second electrical current signal on the tissue structures surrounding it and measure electrical potential through the composite probe and then create an image based on the measured data, that is, a second electrical current can be injected by the plurality of electrodes 308' on the tissue structures surrounding the electrode (308'), and electrical potential is measured and process to create the second image that delineates the tissue structures surrounding the second composite probe 306', thereby determining the boundary of the stimulation target based on both the first and the second images. The generation of the second image need not only be based on electrical current injected and potential measured by the second composite probe alone, but by all the electrodes on both the first and the second composite probes at the same time. With increasing the number of stimulating electrodes, the boundary of the stimulation target can be more clearly defined.

Figure 4A:
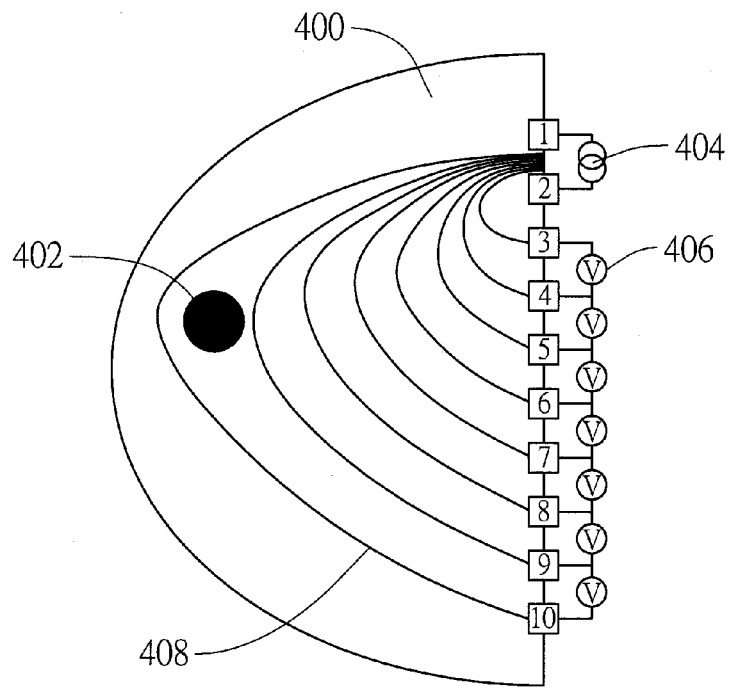
FIGS. 4A and 4B are cross-sectional diagrams showing electrical stimulation implemented by the composite probe according to an embodiment of the present invention.
Figure 4B:
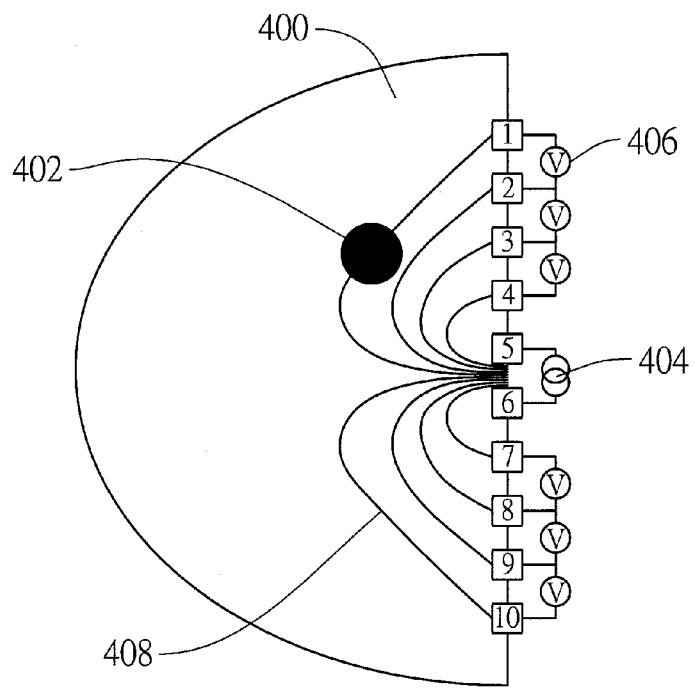

Now referring to FIGS. 4A and 4B, details of the electrical current injected into the tissues structures surrounding the stimulation target and electrical potential measured by the first and the second composite probes are described.

As shown in FIG. 4A, electrodes 1 to 10 are arranged in an array and disposed on a composite probe (it can be considered as either the first or the second composite probe), and the composite probe is implanted into a specific region 400 (which can be considered as the thalamus 300), a current source 404 (which can be considered as the signal generator 312) inputs signals to the specific region 400 via the electrodes 1 and 2 on the electrode array, and a voltage measuring device 406 (which can be considered as the signal receiver 314) measures the electrodes 3 to 10, respectively.

Since a target 402 (which can be considered as the stimulation target, STN 302) exhibits a different electrical characteristic when compare with the background 400, there are change in equipotential lines 408 due to the presence of the target 402 between the plurality of electrodes, and they are reflected on the measured electrical potential in electrodes 3 to 10 of the electrode array, respectively. The voltage measuring device 406 (which can be considered as the signal receiver 314) can obtain measurements by receiving signals from the electrodes 3 to 10. Meanwhile, the impedance of the target 402 in the specific region 400 can be calculated for subsequent image conversion process to reconstruct the image, position or shape of the target 402 in the specific region 400. Specifically, this kind of measuring obtains the impedance of the cross section of the target 402 and the background region 400.

Moreover, as shown in FIG. 4B, the current source 404 may also inputs signals to the specific region 400 via the electrodes 5 and 6 on the electrode array. Similarly, the target 402 which exhibits a different electrical characteristic compare with the background 400 will affect the potential distribution, which are reflected on the electrodes 1 to 4 and 7 to 10 on the electrode array as equipotential lines 408. The voltage measuring device 406 (which can be considered as the signal receiver 314) may also obtain measurements by receiving signals from the electrodes 1 to 4 and 7 to 10. Then, the impedance of the cross section of the target 402 and the region 400 is known, and image conversion process can be performed to achieve imaging of the tissue structures.

More specifically, given that a composite probe has N electrodes, and when the present invention is implemented, matrix analysis and calculation may selectively be performed on the generated signals and received signals using the following formula to obtain the distributions of the conductivity and permittivity in the tissues surrounding the electrodes. Based on the distributions of the conductivity and permittivity, a relevant electrical impedance tomography device (not shown) may then delineate the tissue structures around the electrodes.

For example, in actual calculations, any actual image reconstruction method can selectively uses discrete data by measuring discrete values from electrodes. For N electrodes, $N(N-1)/2$ independent boundary measurements are required (if some input electrodes are not used, the number of measurements will be less than this). The reconstructed image will include a set of discrete pixels, and two sets of measurements may easily represent, through matrix transformation, the relationship between the vector of the transfer impedance z and the image vector of the conductivity c, as indicated by formula (1): $z=T(c)c$. More specifically, transfer impedance is the measured voltage divided by the applied current between a pair of electrodes (or between an electrode and a normal reference point). Generally, the matrix T depends on the distribution of the conductivity and the applied current or voltage. The distribution of the conductivity can be calculated using the improved Newton-Raphson method. In the $k^{th}$ stage, that is, in the iteration process, the conductivity, which is related to the boundary voltage, can be obtained by formula (2): $v=F(c)$. Then, based on formula (3): $c^{k+1}=c^k+\Delta c$, an estimation of the $(k+1)^{th}$ conductivity can be calculated, wherein $\Delta c=\{[F'(c^k)]^t F'(c^k)\}^{-1} F'(c^k)[F(c^k)-v_0]$, $v_0$ is the measured voltage, and $F'(C^K)$ is the Jacobian matrix $[F']_{ij}=df_i/d_j$. The above algorithm provides a good initial estimation of the conductivity, and ensures a sufficient convergence. In addition, the above algorithm can actually be applied, using highly efficient finite elements to calculate forward transformation and direct differentiation of the Jacobian matrix, which mainly involves the inverse matrix of $\{[F'(c^k)]^t F'(c^k)\}$ and the necessary normalization technique, these are not further described.

Figure 5A:
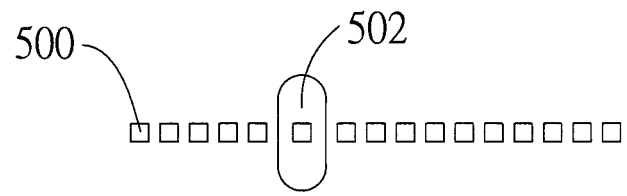
FIGS. 5A and 5B are schematic diagrams showing the shapes of the stimulation targets reconstructed from EIT analysis that is performed using the measurements from the composite probe according to an embodiment of the present invention.
Figure 5B:
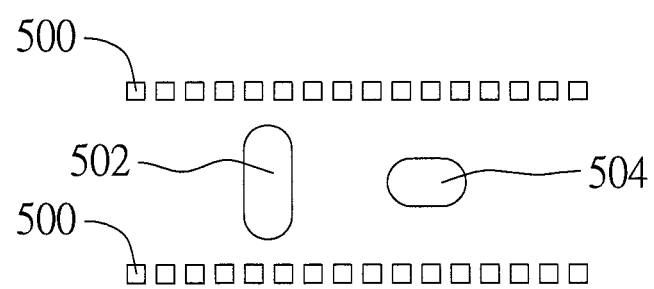

Referring now to FIGS. 5A and 5B, diagrams depicting a plurality of electrodes and implementation details of brain tissue structures surrounding the electrodes to illustrate the case in which there are more than one targets: one could be the stimulation target while the other is a navigation landmark in identifying the stimulation target.

As shown in FIG. 5A, assuming that a composite probe (which can be considered as the first composite probe) has 16 electrodes 500 thereon and is implanted into a specific region. The conductivity σ of the region surrounding the electrodes 500 is 1.0 S/m, and the conductivity σ of a conductive target 502 (the abovementioned stimulation target) is 0.7 S/m. After the voltage and current on each electrode 500 are obtained, EIT analysis is performed to obtain the impedance array as described in above formula (1), and the distributions of the conductivity is established and used to depict a first image of the tissue structure around the composite probe, that is, the shape or location of the conductive target 502, thereby obtaining the precise location of the composite probe within the stimulation target.

As shown in FIG. 5B, assuming that two composite probes (which can be considered as the first composite probe and the second composite probe) has 16 electrodes 500 each and are implanted into a specific region in parallel. The conductivity σ of the region surrounding the electrodes 500 is 1.0 S/m, the conductivity σ of the conductive target 502 (the first stimulation target) is 0.7 S/m, and the conductivity σ of a conductive target 504 (the second stimulation target or navigation landmark) is 1.3 S/m. After the voltage and current on each electrode 500 are obtained, matrix analysis and calculation are performed, that is, the impedance array as described in the above formula (1) is used to further establish the distributions of the conductivity. Consequently, the shapes or locations of the conductive targets 502 and 504 (the second image) can be precisely delineated, so that the boundary of the stimulation targets or navigation landmarks and the precise locations of the two composite probes within or outside the respective stimulation targets or navigation landmarks are determined.

It should be noted that when the techniques of the present invention is actually implemented in a DBS surgery, once the first or the second composite probe has reached the stimulation target and the target boundary is drawn, the composite probe can be taken out, and a permanent wire is implemented to or close to the optimal location of the stimulation target, thereby the efficacy of the surgery can be maximized. Moreover, the techniques disclosed herein allows the DBS surgeons to accurately and quickly determine the target location within the stimulation target, speeding up the progress of the surgery, saving the strength of the patient and reduce chance of complication of the surgery.

In addition, in order to accommodate for different precision requirements, a third composite probe (not shown) that is structurally similar to the first and the second composite probes can be simultaneously or sequentially implanted. In other words, the third composite probe can be implanted along another trajectory which is obtained based on the first and the second images of the tissue structures surrounding the first and the second composite probes. Microelectrode recording signals are then obtained in a similar method to that for the first composite probe, and these microelectrode recording signals are used to guide the third probe to a predefined depth of a corresponding stimulation target. Thereafter, a third electrical current is injected and electrical potential is measured via the third composite probe (or using the three composite probes all together) on the tissue structures surrounding the implantation location, which is then undergone the image conversion process to generate a third image of the tissue structures surrounding the third composite probe. Meanwhile, the boundary of the stimulation target is precisely delineated based on the first, the second and the third images.

Similarly, the step of converting the first, the second and the third electrical signals measured into images, a current, voltage and impedance characteristic analysis of the specific region can first be performed based on the first, the second and the third electrical signals measured; then the result of the current, voltage and impedance characteristic analysis is used to generate the first, the second or the third image that delineates the tissue structures surrounding the first, the second or the third composite probe. However, the details of the third composite probe are similar to those of the first and the second composite probes described before, and so they will not be further described.

It should be noted that the existing electrical impedance tomography (EIT) technique has similarities with the image conversion process of the present invention, but the image conversion process of the present invention is based on injecting electrical current on the tissues of the patient by the probes, and measurements of the electrical potential through the electrodes on the probe, thus differs from the existing EIT technique, which involves surrounding the target within a region with electrodes and delineating the location of the target within the region surrounded by the electrodes. In addition, the method for identifying the stimulation target is not limited to the brain stimulation such as deep brain stimulation and cochlear implants, but also to other fields such as the spinal cord stimulation and the vagus nerve stimulation. In other words, the abovementioned specific region is not limited to the brain region.

In addition, in the method for identifying the stimulation target of the present invention, a plurality of composite probes can be implanted at the same time and the electrical impedance tomography (EIT) analysis is performed. For example, after a first implantation trajectory is obtained based on Computed Tomography (CT) scanning and Magnetic Resonance Imaging (MRI), up to two, three, four or five composite probes can be implanted simultaneously to get microelectrode recording signals from the plurality of composite probes, and these microelectrode recording signals are used to guide the plurality of composite probes to predefined depths of corresponding stimulation targets. Thereafter, electrical current can be injected into and electrical potential are measured via the implanted composite probes on the surrounding tissue structures which are subsequently converted by an image conversion process into images of the tissue structures surrounding the plurality of composite probes. Finally, the boundaries of the stimulation targets are precisely delineated based on the plurality of images delineating the tissue structures surrounding the plurality of composite probes, and the precise locations of the plurality of composite probes in the stimulation targets are also determined. The details of this are similar to the earlier embodiment in which composite probes are not simultaneously implanted, so they will not be further described.

Moreover, after a first electrical current is injected and electrical potential measured is performed by an implanted composite probe, the composite probe can be minutely shifted and the electrical stimulation is performed again, thereby increasing the quantity of data for subsequent image conversion.

Figure 6A:
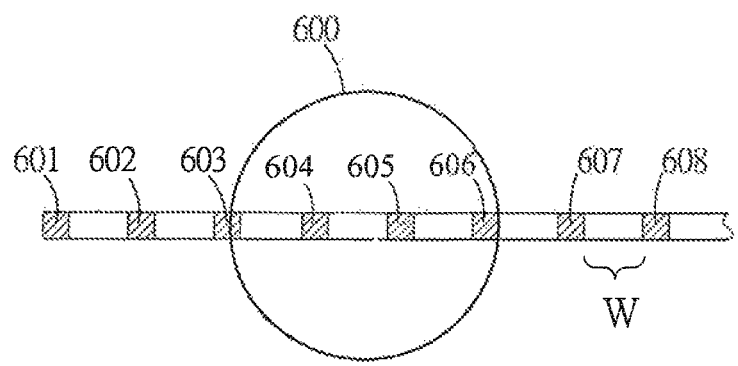
FIGS. 6A and 6B are schematic diagrams showing backward or forward shifting movement of the composite probe by a certain distance in order to inject electrical current and measure electrical potential and process according to an embodiment of the present invention.
Figure 6B:
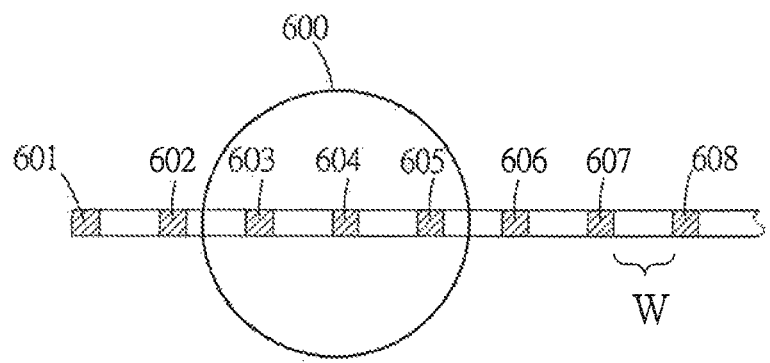

For example, it can be seen from FIGS. 6A and 6B that electrodes 601, 602, 603, 604, 605, 606, 607, and 608 of a composite probe have the same interval W. Assuming the composite probe as shown in FIG. 6A is implanted to a specific region 600 and performs a first electrical current injection and potential measurement, the composite probe afterward is shifted backward (or forward) by a specific distance that is less than the interval W to a position as shown in FIG. 6B. Then, the electrical current injection and potential measurement are carried out again. Therefore, by performing the first electrical measurement and the second electrical measurement, the data source for image conversion is increased, and the resolution and accuracy of the depicted image are improved.

In actual implementations, the composite probe may be shifted and electrical measurements are repeated several times. For example, the composite probe is shifted nine times, each by one tenth of the interval W each time, and nine set of electrical measurements are performed, thus nine times of the electrical signals measurements are obtained. On the other hand, the result of shifting the composite probe and performing electrical measurements several times is effectively equal to that obtained by increasing the number of electrodes in the composite probes equal number of times.

In summary, the present invention proposes a method for location targets of stimulation applicable to a DBS surgery, which requires only a few (or probably one or two) composite probes to accurately and quickly determine the boundary of the DBS stimulation target, which is useful in the implantation of the permanent wire. Therefore, the problem of only the depth of the probe is known (by using MER) but not the precise location of the probe within the stimulation target in the prior art is solved, and also the problem of multiple implantations in the existing techniques is eliminated, speeding up the time taken for the surgery and increasing efficacy of the operation.

The above embodiments are only used to illustrate the principles of the present invention, and they should not be construed as to limit the present invention in any way. The above embodiments can be modified by those with ordinary skill in the art without departing from the scope of the present invention as defined in the following appended claims.

What is claimed is:

1. A method for identifying a boundary of a stimulation target, comprising the steps of:
    (1) performing Computed Tomography (CT) scanning and Magnetic Resonance Imaging (MRI) on a specific region inside a patient to obtain a first implantation trajectory for the specific region;
    (2) arranging a plurality of electrodes on a first composite probe, and implanting the first composite probe into the specific region based on the first implantation trajectory to obtain microelectrode recording signals via the first composite probe, thereby enabling the first composite probe to be guided into a predefined depth within the stimulation target of the patient based on the microelectrode recording signals;
    (3) enabling the electrodes arranged on the first composite probe to inject a first electrical current into tissue structures surrounding the first composite probe and using the first composite probe to measure a first electrical potential, enabling the first composite probe to shift forward or backward along the first implantation trajectory at a predetermined distance, and thereby a second electrical current is injected into and a second electrical potential is measured for the tissue structures surrounding the first composite probe, and converting the first and second electrical potentials into a first image that delineates the tissue structures surrounding the electrodes arranged on the first composite probe;
    (4) reconstructing an image, position or shape of the stimulation target according to discrete data by measuring discrete values from the electrodes and a plurality of independent boundary measurements of the electrodes; and
    (5) identifying the boundary of the stimulation target and pin-pointing a location of the first composite probe implanted within or outside the stimulation target according to the first image.

2. The method for identifying a boundary of a stimulation target of claim 1, wherein the first composite probe includes at least one microelectrode recording signal sensor for providing the microelectrode recording signals and the plurality of electrodes for injecting the first electrical current and measuring the first electrical potential.

3. The method for identifying a boundary of a stimulation target of claim 1, wherein the plurality of electrodes form an electrode array.

4. The method for identifying a boundary of a stimulation target of claim 1, wherein the step (3) further comprising:
    enabling a second composite probe to be implanted into the specific region in parallel with a second implantation trajectory according to the first image of the tissue structures surrounding the first composite probe, and thereby to be guided into the predefined depth within the stimulation target of the patient in the step (2); and enabling the second composite probe to inject a second electrical current into the tissue structures surrounding the second composite probe and using the second composite probe to measure a second electrical potential, and converting the second electrical potential into a second image that delineates the tissue structures surrounding the second composite probe; and the step (5) further comprising identifying the boundary of the stimulation target and pin-pointing locations of the first and the second composite probes implanted within or outside the stimulation target according to the first and the second images.

5. The method for identifying a boundary of a stimulation target of claim 4, wherein the second image is generated by processing the electrical potentials measured by the first and the second composite probes.

6. The method for identifying a boundary of a stimulation target of claim 4, wherein the second composite probe is the same as the first composite probe in structure.

7. The method for identifying a boundary of a stimulation target of claim 4, wherein converting the electrical potentials measured by the first and the second composite probes further comprises:

performing a first current, voltage and impedance characteristic analysis on the specific region based on the electrical currents injected and the electrical potentials measured by the first and the second composite probes; and using a result of the first current, voltage and impedance characteristic analysis to generate the first and the second images that delineate the tissue structures surrounding the first and the second composite probes.

8. The method for identifying a boundary of a stimulation target of claim 4, wherein the step (3) further comprises:

enabling a third composite probe to be implanted into the specific region in parallel with the second implantation trajectory according to the first and second images of the tissue structures surrounding the first and second composite probes, and thereby to be guided into the predefined depth within the stimulation target of the patient in the step (2); and enabling the third composite probe to inject a third electrical current into the tissue structures surrounding the third composite probe and using the third composite probe to measure the third electrical potential, and converting the third electrical potential into a third image that delineates the tissue structures surrounding the third composite probe; and the step (5) further comprising identifying the boundary of the stimulation target and pin-pointing locations of the first, the second and the third composite probes implanted within or outside the stimulation target according to the first, the second and the third images.

9. The method for identifying a boundary of a stimulation target of claim 8, wherein the third image is generated by processing electrical potentials measured by the first, the second and the third composite probes.

10. The method for identifying a boundary of a stimulation target of claim 8, wherein a structure of the third composite probe is the same as structures of the first and the second composite probes.

11. The method for identifying a boundary of a stimulation target of claim 8, wherein converting the electrical potentials measured by the first, the second and the third composite probes comprises:

performing a second current, voltage and impedance characteristic analysis on the specific region based on the electrical currents injected and the electrical potentials measured by the first, the second and the third composite probes; and using a result of the second current, voltage and impedance characteristic analysis to generate the first, the second and the third images that delineate the tissue structures surrounding the first, the second and the third composite probes.

12. The method for identifying a boundary of a stimulation target of claim 1, wherein the predetermined distance is smaller than an interval between the plurality of electrodes of the first composite probe.

13. The method for identifying a boundary of a stimulation target of claim 1, wherein the specific region is a brain region.

14. A method for identifying a boundary of a stimulation target, comprising the steps of:

(1) performing Computed Tomography (CT) scanning and Magnetic Resonance Imaging (MRI) on a specific region inside a patient to obtain a first implantation trajectory for the specific region;

(2) arranging a plurality of electrodes on each of a plurality of composite probes, and implanting the plurality of composite probes into the specific region based on the first implantation trajectory to obtain microelectrode recording signals via the plurality of composite probes, thereby enabling the plurality of composite probes to be guided into predefined depths within the stimulation target of the patient based on the microelectrode recording signals;

(3) enabling the electrodes arranged on each of the plurality of composite probes to inject a plurality of electrical currents into tissue structures surrounding the plurality of composite probes and using the plurality of composite probes to measure a plurality of electrical potentials, and converting the plurality of electrical potentials into a plurality of images that delineate the tissue structures surrounding the electrodes arranged on each of the composite probes, wherein one of the plurality of electrical potentials is measured for the tissue structures surrounding the plurality of composite probes by enabling one of the plurality of composite probes to shift forward or backward along the first implantation trajectory at a predetermined distance;

(4) reconstructing an image, position or shape of the stimulation target according to discrete data by measuring discrete values from the electrodes and a plurality of independent boundary measurements of the electrodes; and (5) identifying the boundary of the stimulation target and pin-pointing locations of the composite probes implanted within or outside the stimulation target according to the plurality of images.

\* \* \* \* \*